(12) United States Patent
Kimmig et al.

(10) Patent No.: US 11,471,690 B2
(45) Date of Patent: Oct. 18, 2022

(54) METHOD FOR PRODUCING A HEAD PART OF AN IMPLANTABLE MEDICAL DEVICE

(71) Applicant: Neuroloop GmbH, Freiburg (DE)

(72) Inventors: Fabian Kimmig, Freiburg (DE); Tim Boretius, Freiburg (DE)

(73) Assignee: NEUROLOOP GMBH, Freiburg (DE)

( * ) Notice: Subject to any disclaimer, the term of this patent is extended or adjusted under 35 U.S.C. 154(b) by 226 days.

(21) Appl. No.: 16/772,040

(22) PCT Filed: Nov. 20, 2018

(86) PCT No.: PCT/EP2018/081922
§ 371 (c)(1),
(2) Date: Jun. 11, 2020

(87) PCT Pub. No.: WO2019/115176
PCT Pub. Date: Jun. 20, 2019

(65) Prior Publication Data
US 2020/0360701 A1 Nov. 19, 2020

(30) Foreign Application Priority Data
Dec. 11, 2017 (DE) ...................... 10 2017 222 364.2

(51) Int. Cl.
*A61N 1/375* (2006.01)
*A61N 1/39* (2006.01)
(Continued)

(52) U.S. Cl.
CPC .......... *A61N 1/3754* (2013.01); *A61N 1/3956* (2013.01); *B29C 39/10* (2013.01);
(Continued)

(58) Field of Classification Search
CPC ...... A61N 1/36; A61N 1/3752; A61N 1/3754; A61N 1/3956; B29C 39/10; B29C 45/14;
(Continued)

(56) References Cited

U.S. PATENT DOCUMENTS

| | | |
|---|---|---|
| 8,267,708 B1 | 9/2012 | Sochor |
| 2002/0035896 A1* | 3/2002 | Jones .................. B25B 27/0014 81/53.2 |

(Continued)

FOREIGN PATENT DOCUMENTS

| | | |
|---|---|---|
| DE | 102012010901 A1 | 12/2012 |
| DE | 202013012073 U1 | 3/2015 |
| EP | 2134418 B1 | 6/2012 |

OTHER PUBLICATIONS

International Search Report for PCT/EP2018/081922, dated Jan. 31, 2019; English translation submitted herewith (5 pgs.).

*Primary Examiner* — George Manuel
(74) *Attorney, Agent, or Firm* — Fitch, Even, Tabin & Flannery LLP

(57) ABSTRACT

A method for producing a head part of an implantable medical device is described, with a head part housing, which has a recess in the form of a blind hole, along which at least one electrically conducting contact ring element, together with an electrically insulating, elastically deformable sealing ring, are joined together in a force fit in a coaxial arrangement and an axial serial sequence under an axial joining force. The method is characterized in that the generation of the joining force between the at least one contact ring element and the sealing ring is executed along the assembly tool by use of means of attachment fitted on both sides of the at least one contact ring element and the sealing ring along the assembly tool, of which at least one means of attachment is axially movably and detachably fixed in an axially secure manner to the assembly tool.

11 Claims, 1 Drawing Sheet

(51) Int. Cl.
*B29C 39/10* (2006.01)
*H01R 13/52* (2006.01)
*H01R 24/58* (2011.01)
*B29L 31/00* (2006.01)

(52) U.S. Cl.
CPC ....... *H01R 13/521* (2013.01); *H01R 13/5224* (2013.01); *H01R 24/58* (2013.01); *B29L 2031/753* (2013.01)

(58) Field of Classification Search
CPC ............ B29L 2031/753; H01R 13/521; H01R 13/5224; H01R 24/58
See application file for complete search history.

(56) References Cited

U.S. PATENT DOCUMENTS

2015/0142092 A1    5/2015   Vadlamudi et al.
2016/0100887 A1    4/2016   Wu et al.

\* cited by examiner

METHOD FOR PRODUCING A HEAD PART OF AN IMPLANTABLE MEDICAL DEVICE

CROSS REFERENCE TO RELATED APPLICATIONS

Reference is made to PCT/EP2018/081922 filed Nov. 20, 2018, designating the United States, which claims priority to German Application No. 10 2017 222 364.2 filed Dec. 11, 2017, which are incorporated herein by reference in their entirety

BACKGROUND OF THE INVENTION

Field of the Invention

The invention relates to a method for producing a head part of an implantable medical device, with a head part housing which has a blind hole recess, along which, in a coaxial arrangement and in an axial serial sequence, at least one electrically conducting contact ring element, together with an electrically insulating, elastically deformable sealing ring, are joined together in a force fit under an axial joining force.

Description of the Prior Art

Implantable medical devices for purposes of electrical stimulation of local intracorporeal regions, short implantable pulse generators (IPGs), for example, for cardiotherapeutic defibrillation, pacemaker and resynchronisation applications, for neurostimulation therapeutic measures, such as for example spinal cord stimulation, brain stimulation, or vagus nerve stimulation, to name but a few, usually have a self-contained housing, in which are contained components for electrical pulse generation, such as at least one electrical energy source and an electrical circuit structure connected to the latter. In addition, the housing is adjoined by a so-called head part, in which is contained an electrical contact arrangement, which is electrically connected to at least one of the energy source and the electrical circuit structure, and into which a connector arrangement can be introduced, which is sealed with the head part in a manner impermeable to fluids. The connector arrangement is in contact with electrical supply and discharge lines for purposes of intracorporeal local application of the electrical stimulation signals, and if necessary, the supply of intracorporeally locally tapped electrical signals to the electrical circuit structure that is present in the housing.

The publication EP 2 134 418 B1 describes a generic head part of an implantable medical device, which comprises two head part housing halves, which can be joined together along a joining seam, into each of which housing halves half-cylindrical recesses are introduced in a serial sequence, spaced apart by partitions, into each of which recesses are introduced electrically conducting contact ring elements and electrically insulating sealing rings in an serially alternating sequence. The head part, assembled from the two head part housing halves, thus comprises an arrangement of coaxially aligned and electrically insulated contact ring elements, for purposes of making electrical contact with which lateral access is provided in the head part, through which an electrical connector arrangement can be introduced, in a manner impermeable to fluids, into a cavity that is surrounded by all the annular contact ring elements.

The publication DE 10 2012 010 901 A1 discloses a method for the positioning and holding of electrical contacts and seals within a head part for purposes of making electrical contact with a medical implantable device. In the head part housing, which is a biocompatible and electrically insulating material, a bore in the form of a blind hole is introduced at one side, into which are introduced electrically conducting contact rings and annular sealing elements in an alternating sequence, which together surround a cavity, into which a rod-shaped connector arrangement can be introduced. Each of the individual annular contact rings inside the head part is connected via an electrical connection line to electrical components that are located inside the housing of the medical implantable device.

For purposes of achieving a seal that is impermeable to fluids and as durable as possible, together with the electrical insulation of the individual electrical contact ring elements from one another, the alternating sequence of electrical contact ring elements and sealing rings must be fixed within the head part with a greatest possible axial joining force. This requires complex assembly measures, which can usually only be carried out manually, and only with considerable dexterity.

In the publication DE 20 2013 012 073 U1, a connector bore module assembly is disclosed, for the assembly of which a number of contact rings and sealing elements are arranged in an alternating sequence along a rod-shaped assembly tool. By use of a clamping device, all the contact rings and sealing elements seated along the assembly tool are clamped together under the application of an axial joining force. For purposes of conserving the joining force, a sleeve element is used, which is seated on the assembly tool in an axially secure manner by use of a grub screw, and which, together with an assembly tool head at one end, bounds the arrangement of contact rings and sealing elements axially at both ends. In this clamped state, the arrangement is encapsulated with a curable casting compound, which in the solidified state hosts the joining force.

SUMMARY OF THE INVENTION

The object underlying the invention is the further development of a method for producing a head part of an implantable medical device, with a head part housing, which possesses a recess in the form of a blind hole, along which, in a coaxial arrangement and in an axial serial sequence, at least one electrically conducting contact ring element, together with an electrically insulating, elastically deformable sealing ring, are joined together in a force fit under an axial joining force, such that the procedural complexity, together with the expenditure in terms of time and cost, for the production of both individually assembled head parts, and also head parts produced in large quantities, are to be significantly reduced. Furthermore, it is of particular concern that the quality of manufacture, together with the impermeability to fluids, and the associated service life of a head part, must satisfy the highest requirements.

The method in accordance with the invention for the production of a head part of an implantable medical device, is composed of the following method steps.

At least one electrically conducting contact ring element, together with at least one electrically insulating sealing ring, of an elastically deformable material, are arranged along a rod-shaped assembly tool, which is preferably designed as a rod, bar or pin. The arrangement is effected simply by the threading of what is preferably a large number of contact ring elements and sealing rings onto the rod-shaped assembly tool, in each case in a serially alternating sequence between contact ring elements and sealing rings.

The at least one contact ring element, together with the at least one sealing ring, are then joined together, that is to say, with one another, in a force fit by use of a joining force oriented along the rod-shaped assembly tool. By this force fit the at least one electrically insulating and elastically deformable sealing ring sits tightly against a surface of the electrically conducting contact ring element that is facing the sealing ring, thereby forming an annular force-loaded joint that is impermeable to fluids.

For purposes of generating the joining force acting axially between the at least one contact ring element and the sealing ring along the rod-shaped assembly tool, the attachment parts are fitted along the assembly tool on both sides of the at least one contact ring element and the sealing ring. At least one means of attachment is axially moveably and detachably fixed in an axially secure manner on the assembly tool, and is designed in the form of a nut with an internal thread, which is brought into engagement with an external thread provided along the assembly tool, such that the means of attachment, which is designed in the form of a nut, by relative rotation along the external thread of the assembly tool, thereby forms the joining force, and is brought into engagement in a force fit with the at least one contact ring element or sealing ring on one side. The relative longitudinal adjustability of the means of attachment along the assembly tool, contingent on the threaded engagement between the internal thread of the means of attachment, designed in the form of a nut, and the external thread fitted on the assembly tool, enables a fine adjustment of the joining force, which can be generated solely by the rotation of the assembly tool relative to the means of attachment. The assembly tool preferably has a tool head with a tool flange formed at one end, for example, for a detachably secure engagement with a turning tool in the form of a slotted or cross-headed screwdriver, or an Allen key, or similar.

The means of attachment, designed in the form of a nut, can be structurally formed in many different ways. In addition to a traditional nut, a plate element can be provided, with at least one threaded hole with an internal thread. By the provision of two or more threaded holes within a plate element, the number of separate adjacently arranged arrangements, each with a coaxial sequence of contact ring elements and sealing rings, arranged and scaled spatially next to one another within a head part, can be specified as required. In this way, head parts can be designed with a plurality of electrical connection sockets, and this in a compact and easy to implement form of construction. In addition, the use of a plate element enables a specific spatial relative arrangement to be specified between two or more electrical connection sockets arranged within a head part. By a dimensioning of the axial thread lengths of the internal and external threads such that they match each other, and an associated maximum specifiable rotation of the assembly tool into the internal thread of the means of attachment, a defined specifiable maximum joining force between the contact ring elements and sealing rings can be structurally specified, as a result of which the assembly process can be executed in a reliable and reproducible manner.

In a preferred form of embodiment, the rod-shaped assembly tool has at its head end a mechanical stop which is connected to the latter in an axially secure manner, and which is connected to the assembly tool in a detachably secure, or integral manner, against one side of which stop the axially stacked arrangement, having the at least one contact ring element together with the sealing ring, sits in a supported manner. Located opposite the mechanical stop for the axially stacked arrangement is fitted the means of attachment in the form of a nut, which can be moved along the rod-shaped assembly tool and can be axially detachably and securely connected to the assembly tool.

The above assembly tool, prefabricated with the at least one electrically conducting contact element and the at least one sealing ring, represents a semi-finished product that can be handled as a unit, and which in a further method step is encapsulated with a casting compound. For this purpose, the at least one contact ring element arranged along the rod-shaped assembly tool, and the at least one sealing ring, which are joined together in a force fit, are encapsulated with a solidifiable casting compound present in a flowable form. By virtue of the mutual joining of the at least one contact ring element with the sealing ring in a form fit, in a manner impermeable to fluids, the flowable casting compound cannot penetrate into the interior space enclosed collectively by the at least one contact ring element and sealing ring.

The casting compound is preferably a biocompatible plastic or a resin compound, preferably an epoxy, which after a short time solidifies completely, thereby forming a dimensionally stable body. After the casting compound has solidified, the rod-shaped assembly tool is finally released and removed from the at least one contact ring element and the sealing ring. The axial joining force acting between the at least one contact ring element and the sealing ring remains unchanged, and is fully hosted by the solidified casting compound in the form of a dimensionally stable matrix forming at least one part of the head part housing. The means of attachment designed in the form of a nut remains in the solidified casting compound.

In order to facilitate the release and removal of the assembly tool from the head part, the end of the assembly tool, protruding through the internal thread of the means of attachment designed in the form of a nut, is wetted with a protective compound, preferably silicone or similar, prior to the casting with the flowable casting compound. This prevents the solidified casting compound from forming a firm bond with the protruding assembly tool end section.

BRIEF DESCRIPTION OF THE DRAWINGS

The invention will be described below in an exemplary manner by way of examples of embodiment with reference to the figures, without any limitation of the general inventive concept. Here.

DETAILED DESCRIPTION OF THE INVENTION

Figure 1:
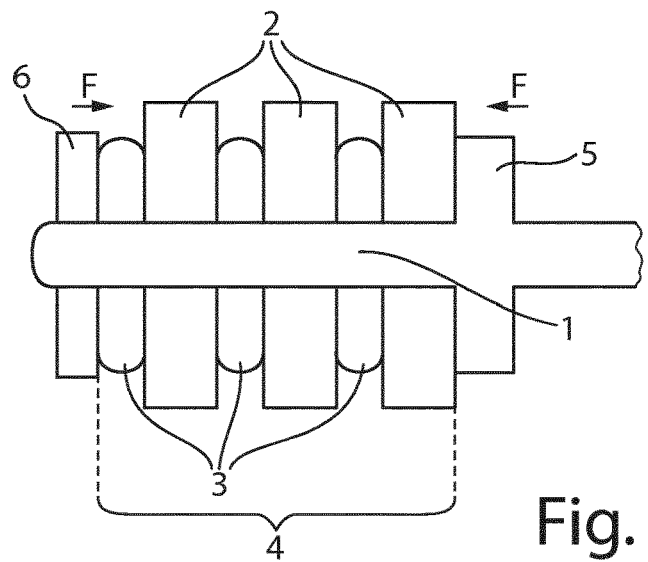
FIG. 1 shows a schematic representation of an axially stacked arrangement of contact ring elements and sealing rings along a rod-shaped design of assembly tool, FIGS. 2a and b show detailed views of the design of a means of attachment that can be detachably fitted in an axially secure manner along the rod-shaped assembly tool.

FIG. 1 illustrates schematically a rod-shaped assembly tool 1, along which electrically conducting contact ring elements 2 and electrically insulating sealing rings 3 made of an elastomer material are arranged in an axially serially alternating sequence. On both sides of the axially stacked arrangement 4 composed of the alternating sequence of contact ring elements 2 and sealing rings 3, means of attachment 5, 6 are fitted along the rod-shaped assembly tool 1. In the case of the means of attachment 5 shown in FIG. 1, this takes the form of a mechanical stop, designed as a plate or disc, which is connected to the otherwise rod-shaped design of assembly tool 1, and which is connected integrally with the assembly tool; on one side the axially stacked arrangement 4 is directly adjacent to the stop. The means of attachment 6 arranged opposite to the latter along the axially stacked arrangement 4 is designed such that it can move axially along the rod-shaped assembly tool 1, and moreover has a locking mechanism that is capable of fixing the means of attachment 6 such that it is axially secure relative to the rod-shaped assembly tool 1.

Figure 2A:
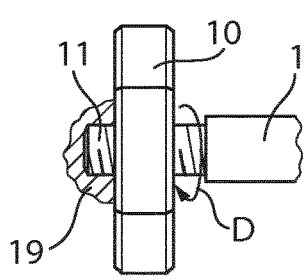
Figure 2B:
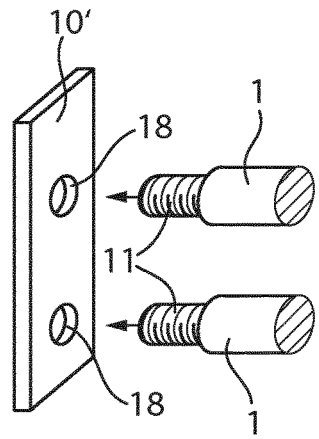

FIGS. 2a and *b* show preferred embodiments for the implementation of the axially movable and axially securely lockable means of attachment 6. FIG. 2a shows a nut 10 with an internal thread, which is in engagement with an external thread 11 provided at one end of the rod-shaped assembly tool 1. The means of attachment 6 designed as a nut 10 does not necessarily have to be designed as a traditional nut; in fact any bodies or body shapes with an internal thread 18 can serve as the means of attachment 6. FIG. 2b illustrates a plate element 10' as a means of attachment 6, which provides two openings arranged adjacent to one another, each with an internal thread 11, into each of which an assembly tool 1 can be brought into engagement by way of its external thread 11. The plate element 10' can be shaped and dimensioned in any two or three-dimensional manner. Furthermore, any number of openings with internal threads 11 can be introduced into the plate element 10'. By this mechanism it is possible to implement a plurality of arrangements within a head part, each consisting of coaxially arranged contact ring elements 2 and sealing rings 3, and each of which serve as electrical plug-in sockets for connector units. Depending on the design of the plate element 10', as well as the number and arrangement of openings provided with internal threads 11 within the plate element 10', head parts of any complexity can be implemented without great production and assembly effort.

For purposes of applying a joining force that is axially oriented to the rod-shaped assembly tool 1, by which the alternating sequence of contact ring elements 2 and sealing rings 3 are joined together, that is to say, with one another, in a force fit, the assembly tool 1 must be rotated relative to the nut 10 or to the plate element 10', for example by the complete rotation of the external thread 11 on the end of the assembly tool into the internal thread 11, as a result of which a defined, specifiable joining force, acting along the contact ring elements 2 and sealing rings 3 that are sitting on the assembly tool, is set. In the simplest case, the relative rotation can be implemented with a rotary tool, e.g. in the form of a spanner, that can be brought into engagement with the assembly tool.

Figure 3:
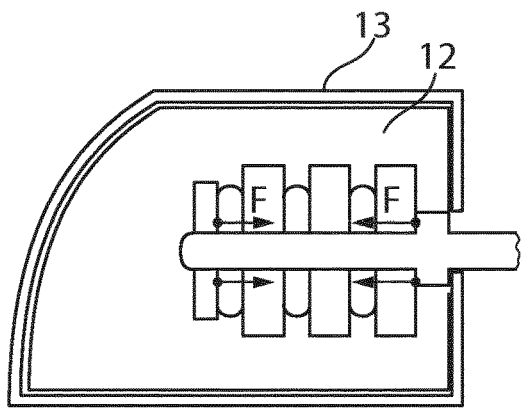
FIG. 3 shows the method step of the encapsulation of the stacked arrangement of contact ring elements and sealing rings fitted on the rod-shaped assembly tool with a casting compound.

The axially stacked arrangement 4 illustrated in FIG. 1, having a number of electrical contact ring elements 2 and sealing rings 3 threaded in an alternating sequence onto the rod-shaped assembly tool 1, which with the aid of the means of attachment 5 and 6 are joined together under the specification of an axially-acting joining force F, represents a semi-finished product to be handled manually or automatically as a unit, which is then encapsulated with a solidifiable casting compound 12 in a flowable form in the manner shown in FIG. 3. A casting mould 13, into which the above-cited semi-finished product with the axially preloaded contact ring elements and sealing rings, together with the assembly tool, is introduced, serves this purpose in an advantageous manner. The casting mold 13 is then filled with a flowable casting compound 12, wherein the casting compound 12 surrounds the entire stacked arrangement 4, that is the means of attachment 6 as well as all contact ring elements and sealing rings, and preferably also at least partially surrounds the means of attachment 5.

Figure 4:
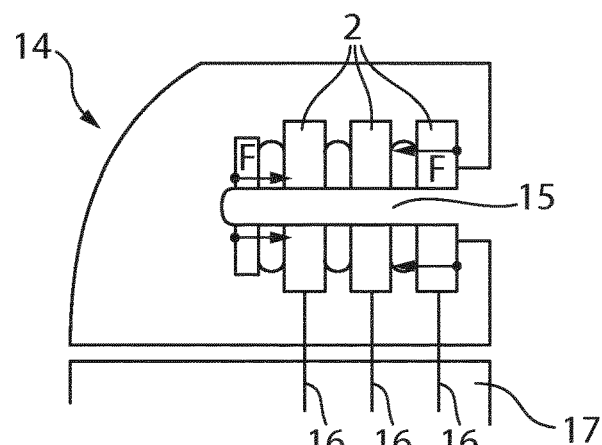
FIG. 4 shows a representation of the solidified casting compound with the enclosed stacked arrangement of contact ring elements and sealing rings.

After the casting compound 12 has solidified, the assembly tool 1 is removed as shown in FIG. 4, wherein the means of attachment 6 and the axially stacked arrangement 4 remain in the casting compound 12. If the means of attachment 5 is not integral, as shown in FIG. 1, but is detachably mounted securely on the assembly tool in the same way as the means of attachment 6, the means of attachment 5 can in this case also remain in the cured casting compound.

In order to prevent the end of the assembly tool 1 for protruding beyond the internal thread 18 of the means of attachment 6 from making a firm material bond with the solidified casting compound 12, which would make it at least more difficult to release the assembly tool 1, the end of the assembly tool is wetted with a protective compound 19, for example, silicone or similar, before casting, see FIG. 2a.

After removal of the assembly tool 1, the axial joining force F prevailing between the contact ring elements and sealing rings 1 remains unchanged, in particular because the joining force F is hosted by the solidified casting compound 12. In contrast to the production step illustrated in FIG. 3, in which the joining force F is generated and retained on the two sides by the means of attachments 5 and 6, in the case of FIG. 4, after removal of the assembly tool 1, the joining force F is underpinned or hosted exclusively by the solidified casting compound 12, and remains unchanged by virtue of the dimensional stability of the solidified casting compound.

At the same time, after removal of the assembly tool 12, open access 15 within a cavity is formed within the head part 14 formed by solidification of the casting compound, into which cavity a connector arrangement, not illustrated, can be introduced for purposes of making electrical contact with the individual electrical contact ring elements 2.

An electrical conductor structure 16 also exits from each electrically conducting contact ring element 2; this conductor structure protrudes through the head part 14 on one side and is connected to electrical components within an implantable medical device 17. For this purpose, the electrical conductor structures can already be connected to the respective electrical contact ring elements before the casting of the semi-finished product, and cast together with the described semi-finished product. Alternatively the electrical conductor structures can subsequently make contact with the contact ring elements by the drilling of holes into the cured matrix and the appropriate insertion of the conductor structures into the holes.

As mentioned in the introduction, the implantable medical device 17 is preferably a housed pulse generator for the generation of electrical stimulation signals, which can be applied to certain intracorporeal regions by way of a connector unit, not shown in FIG. 4, and associated electrical lines. The head part 14 is typically attached to the medical device 17 such that it can be detached, and such that a replacement of, for example the pulse generator, is possible without affecting the intracorporeally located electrical lines.

LIST OF REFERENCE SYMBOLS

1 Rod-shaped design of assembly tool
2 Electrically conducting contact ring element 3. Electrically insulating sealing ring
4. Stacked arrangement
5 and 6 Means of attachment
7. Sleeve
8. Hole with internal thread
9. Grub screw
10. Nut
10' Plate element
11. External thread
12. Casting compound
13. Casting mold
14. Head part
15. Cavity, open access
16. Electrical conductor structure
17. Implantable medical device
18. Internal thread
19. Protective compound
D Rotation
F Joining force

The invention claimed is:

1. A method for producing a head part of medical device configured for implantation into a patient, with a head part housing, having a recess which is a blind hole, along which, in a coaxial arrangement and in an axial serial sequence, at least one electrically conducting contact ring element, together with an electrically insulating, elastically deformable sealing ring, are joined together in a force fit under an axial joining force, comprising:

positioning the at least one contact ring element, together with the at least one sealing ring, arranged along a rod-shaped assembly tool, together in a force fit along the rod-shaped assembly tool by generating joining force;

encapsulating at least the at least one contact ring element, arranged along the rod-shaped assembly tool and joined in a force fit together with the at least one sealing ring, with a solidifiable casting compound present in a flowable form;

generating the joining force between the at least one contact ring element and the sealing ring along the assembly tool by use of means of attachment fitted on both sides of the at least one contact ring element and sealing ring along the assembly tool, with at least one means of attachment being axially moveably and detachably fixed in an axially secure manner to the assembly tool, comprising a nut with an internal thread, which is brought into engagement with an external thread provided along the assembly tool, such that the means of attachment, the nut is brought into engagement with the at least one contact ring element or sealing ring by relative rotation along an external thread of the assembly tool in a force fit on one side, to form the joining force, and the rod-shaped assembly tool being released and removed from the at least one contact ring element and the at least one sealing ring after solidification of the casting compound, which forms a dimensionally stable matrix forming at least part of the head part housing, mechanically hosts the axial joining force; and after releasing and removing the assembly tool, at least one means of attachment remains in the solidified casting compound and is configured for implantation.

2. A method according to claim 1, comprising
providing contact ring elements and sealing rings, arranged along the rod-shaped assembly tool in a serially alternating sequence.

3. A method according to claim 2, wherein
before or after the encapsulation and solidification of the casting compound, the at least one contact ring element is connected to at least one electrical conductor structure, which leads out through the casting compound.

4. A method according to claim 3, wherein
encapsulating the at least one contact ring element and sealing ring, which are arranged along the rod-shaped assembly tool and are joined in a force fit, is performed with the a casting mould.

5. A method according to claim 2, wherein
encapsulating the at least one contact ring element and sealing ring, which are arranged along the rod-shaped assembly tool and are joined in a force fit, is performed with the a casting mould.

6. A method according to claim 2, wherein
after releasing and removing of the rod-shaped assembly tool from the at least one contact ring element, together with the sealing ring, forming an open access to a cylindrical volume enclosed by the at least one contact ring element, together with the sealing ring, within the head part.

7. A method according to claim 1, wherein
before or after the encapsulation and solidification of the casting compound, the at least one contact ring element is connected to at least one electrical conductor structure, which leads out through the casting compound.

8. A method according to claim 7, wherein
encapsulating the at least one contact ring element and sealing ring, which are arranged along the rod-shaped assembly tool and are joined in a force fit, is performed with the a casting mould.

9. A method according to claim 1, wherein
encapsulating the at least one contact ring element and sealing ring, which are arranged along the rod-shaped assembly tool and are joined in a force fit, is performed with the a casting mould.

10. A method according to claim 1, wherein
after releasing and removing of the rod-shaped assembly tool from the at least one contact ring element, together with the sealing ring, forming an open access to a cylindrical volume enclosed by the at least one contact ring element, together with the sealing ring, within the head part.

11. A method according to claim 1, wherein
a head part comprising a mechanical and electrical coupling to an implantable medical device in a pulse generator.

* * * * *